United States Patent

Denzel et al.

[11] 4,127,657
[45] Nov. 28, 1978

[54] 4H-PYRAZOLO[1,5-A]PYRAZOLO[4',3':5,6-]PYRIDO[3,4-E]PYRIMIDIN-5(8H)ONE AND DERIVATIVES THEREOF

[75] Inventors: Theodor Denzel, Regensburg; Hans Hoehn, Tegernheim, both of Fed. Rep. of Germany

[73] Assignee: E. R. Squibb & Sons, Inc., Princeton, N.J.

[21] Appl. No.: 829,841

[22] Filed: Sep. 1, 1977

Related U.S. Application Data

[62] Division of Ser. No. 659,291, Feb. 19, 1976, Pat. No. 4,070,466.

[51] Int. Cl.² .................. A61K 31/415; C07D 471/04
[52] U.S. Cl. .................. 424/248.54; 424/251; 544/60; 544/58; 544/115; 544/247
[58] Field of Search ............... 260/256.4 F, 256.5 R; 544/58, 115, 247; 424/248.54, 251

[56] References Cited

U.S. PATENT DOCUMENTS

| | | | |
|---|---|---|---|
| 3,894,021 | 7/1975 | Denzel et al. | 260/256.4 F |
| 4,000,277 | 12/1976 | Denzel et al. | 260/256.4 F |
| 4,061,632 | 12/1977 | Denzel et al. | 260/256.4 F |

Primary Examiner—Donald G. Daus
Assistant Examiner—James H. Turnipseed
Attorney, Agent, or Firm—Lawrence S. Levinson; Merle J. Smith

[57] ABSTRACT

New 4H-pyrazolo[1,5-a]pyrazolo[4',4':5,6]pyrido[3,4-e]pyrimidin-5(8H)one and new derivatives thereof have the general formula

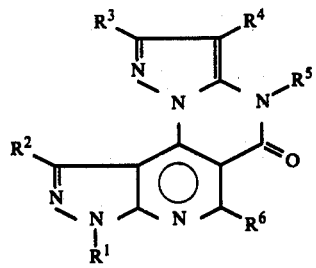

The compounds are useful as anti-inflammatory agents and central nervous system depressants.

10 Claims, No Drawings 4,127,657

4H-PYRAZOLO[1,5-A]PYRAZOLO[4'3':5,6]PYRIDO[3,4-E]PYRIMIDIN-5(8H)ONE AND DERIVATIVES THEREOF

This is a division of application Ser. No. 659,291, filed Feb. 19, 1976, U.S. Pat. No. 4,070,466, Jan. 24, 1978.

SUMMARY OF THE INVENTION

This invention relates to the new compounds 4H-pyrazolo[1,5-a]pyrazolo[4',3':5,6]pyrido[3,4-e]pyrimidin-5(8H)-one, new derivatives and salts thereof. These new compounds have the general formula

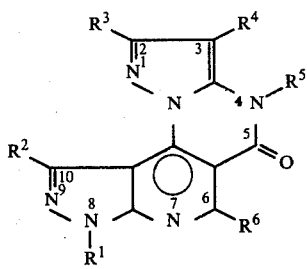

$R^1$ is hydrogen, lower alkyl, phenyl, phenyl-lower alkylene, benzoyl or substituted benzoyl.

$R^2$ is hydrogen or lower alkyl.

$R^3$ is hydrogen, lower alkyl or phenyl.

$R^4$ is hydrogen or lower alkyl.

$R^5$ is hydrogen, lower alkyl, phenyl-lower alkylene, benzoyl or substituted benzoyl, lower alkanoyl, lower alkoxy-lower alkylene, lower alkylthio-lower alkylene, phenyl or substituted phenyl, amino-lower alkylene or di-lower alkylamino-lower alkylene. The basic amino group may also form one of the heterocycles piperidine, morpholine, thiamorpholine or piperazine.

$R^6$ is hydrogen or lower alkyl.

DETAILED DESCRIPTION OF THE INVENTION

The various groups represented by the symbols are of the following types:

The lower alkyl groups are straight or branched chain hydrocarbon groups having up to seven carbon atoms like methyl, ethyl, propyl, isopropyl, butyl, isobutyl, t-butyl, pentyl and the like. The lower alkylene groups are divalent radicals of the same kind. Examples of the phenyl-lower alkylene groups are benzyl, phenethyl, phenylisopropyl and the like. The $C_1$–$C_4$ are especially the $C_1$–$C_2$ lower alkyl and lower alkylene groups are preferred.

The substituted phenyl and substituted benzoyl groups (i.e., $R_9$-phenyl, $R_9$-benzoyl) are simply substituted benzoyl groups having halogen (the four common halogens, but preferably chlorine or bromine), lower alkyl or lower alkoxy (similar to the lower alkyl groups defined above) groups ($R_9$) on the phenyl ring, for example, p-chlorophenyl, o-chlorophenyl, p-bromophenyl, m-chlorophenyl, m-bromophenyl, p-tolyl, o-tolyl, o-ethylphenyl, p-methoxyphenyl, p-chlorobenzyl, o-chlorobenzyl, p-bromobenzoyl, m-bromobenzoyl, p-methylbenzoyl, o-ethylbenzoyl, p-methoxybenzoyl and the like. Chlorine, bromine and methyl are the preferred substituents in both instances.

The lower alkanoyl groups are the acyl groups of the lower ($C_2$–$C_7$) fatty acids, e.g., acetyl, propionyl, butyryl, isobutyryl and the like. Those with up to four carbons in the chain are preferred, especially acetyl.

The lower alkoxy-lower alkylene and lower alkylthio-lower alkylene groups represented by $R^5$ have radicals like those described above including such groups as methoxymethylene, ethoxymethylene, methoxyethylene, methylthiomethylene, methylthioethylene, ethylthiomethylene, ethylthioethylene, etc.

The amino-lower alkylene groups are of the same type, e.g., aminomethyl, aminoethyl, etc. The di-lower alkylamino-lower alkylene groups are also of the same type wherein the nitrogen is substituted with two lower alkyl groups. In addition, the two lower alkyl groups may join in forming a heterocycle which may include an additional hetero atom. In other words, the di-lower alkylamino-lower alkylene group can take the form

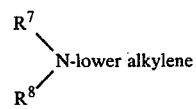

wherein $R^7$ and $R^8$ are lower alkyl groups or join together to complete the heterocycle piperidine, morpholine, piperazine or thiamorpholine (preferably the first three and especially the first two). Preferably the lower alkyl and lower alkylene groups have up to 4 and especially 1 or 2 carbons. Thus, groups like dimethylaminomethyl, diethylaminomethyl, dimethylaminoethyl, diethylaminoethyl, dimethylaminopropyl, piperidinomethyl, piperidinoethyl, morpholinomethyl, morpholinoethyl, thiamorpholinomethyl, thiamorpholinoethyl, piperazinomethyl, piperazinoethyl, piperazinopropyl are included.

Preferably $R^1$ is lower alkyl, especially ethyl; $R^2$ is hydrogen or lower alkyl, especially hydrogen; $R^3$ is hydrogen or lower alkyl, especially methyl; $R^4$ is hydrogen or lower alkyl, especially hydrogen; $R^5$ is lower alkyl, especially methyl, ethyl and isopentyl, or di-lower alkylamino-lower alkylene, especially dimethylaminopropyl and dimethylaminoethyl; $R^6$ is lower alkyl or hydrogen, especially hydrogen.

The products of the examples are representative of the various compounds of this invention and constitute especially preferred embodiments.

The new compounds of formula I are formed by the following series of reactions. The symbols in the structural formulas have the same meaning as previously described.

A pyrazolo[3,4-b]pyridine of the formula

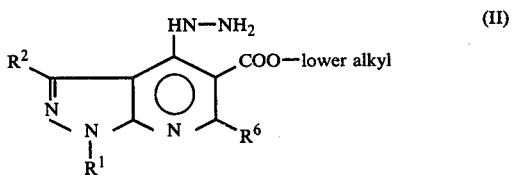

(produced according to the procedure given in U.S. Pat. No. 3,761,487, Sept. 25, 1973) is made to react with an iminonitrile of the formula

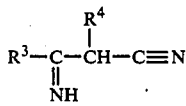

(III)

or a ketonitrile of formula

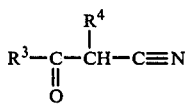

(IV)

in an organic solvent like alcohol, or the like.

By this reaction a hydrazone of the formula

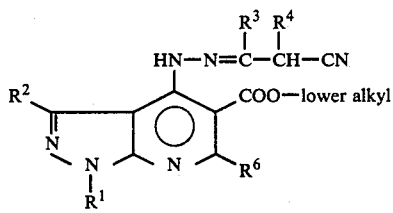

(V)

is produced. A compound of formula I wherein $R^5$ is hydrogen is now obtained by treating the compound of formula V in an organic acid, like acetic acid with zinc chloride or any other Lewis acid as catalyst. Alternatively, the ring closure may be effected under basic conditions, e.g., with an alkali metal alcoholate in the corresponding alcohol like sodium or potassium alcoholate in ethyl alcohol.

Compounds of formula I, wherein $R^5$ is other than hydrogen, are obtained by treatment of a cyclized compound of formula I wherein $R^5$ is hydrogen, obtained as just described, with the halide $R^5$-hal, wherein hal is a halogen, preferably chlorine or bromine, and $R^5$ has the meaning defined above, in the presence of a base, preferably a base of an alkali metal, like sodium hydride, sodium or potassium alcoholate, sodium metal, sodium or potassium hydroxide, or the like, in a solvent like dimethylformamide or diethyleneglycol dimethyl ether.

The new compounds of formula I form salts which are also part of this invention. The salts include acid addition salts, particularly the non-toxic, physiologically acceptable members. These salts are formed by reaction with one or more equivalents of a variety of inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, aryl- and alkanesulfonates like benzenesulfonate, methanesulfonate, cyclohexanesulfamate and toluenesulfonate, etc. The acid addition salts frequently provide a convenient means for isolating the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts can then be formed from the free base by reaction with an equivalent or more of acid containing the desired anion.

Additional experimental details are found in the examples.

The new compounds of this invention have central nervous system depressant activity and can be used as psychotropic agents, e.g., as ataractic agents for the relief of anxiety and tension states, for example, in mice, cats, rats, dogs and other mammalian species. For this purpose a compound or mixture of compounds of formula I, or non-toxic, physiologically acceptable acid addition salt thereof, is preferably administered orally, but parenteral routes such as subcutaneously, intramuscularly, intravenously or intraperitoneally in the described dosages, can also be employed. A single dose, or preferably 2 to 4 divided daily doses, provided on a basis of about 1 to 50 mg. per kilogram per day, preferably about 2 to 15 mg. per kilogram per day, is appropriate.

The new compounds of this invention also have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema or delayed hypersensitivity skin reaction tests in rats.

The compounds of the invention can be utilized by formulation in compositions such as tablets, capsules or elixirs for oral administration or in sterile solutions or suspensions for parenteral administration. About 10 to 250 mg. of a compound or mixture of compounds of formula I or physiologically acceptable acid addition salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propyl parabens as preservatives, a dye and a flavoring such as cherry or orange flavor. Of course, any material used in preparing the dosage unit should be pharmaceutically pure and substantially non-toxic in the amounts employed.

For topical administration as an anti-inflammatory agent, a conventional lotion, ointment or cream containing about 0.1 to 3 percent by weight of a compound of formula I or its salt is formulated.

The following examples are illustrative of the invention and constitute especially preferred embodiments. They also serve as models for the preparation of other members of the group which can be produced by suitable substitution of starting materials. All temperatures are in degrees celsius.

EXAMPLE 1

2,4-Dimethyl-8-ethyl-4H-pyrazolo[1,5-a]pyrazolo[4',3':5,6]-pyrido[3,4-e]pyrimidin-5(8H)-one (a)

4-[2-(2-cyano-1-methylethylidene)hydrazino]-1-ethyl-1H-pyrazolo[3,4-e]pyridine-5-carboxylic acid, ethyl ester 660 g. of 1-ethyl-4-hydrazino-1H-pyrazolo[3,4-b]-pyridine-5-carboxylic acid, ethyl ester (3 mol.) and 246 g. of 3-iminobutyronitrile (3 mol.) are refluxed with stirring in 3 liters of butanol for 12 hours. The solvent is distilled off and the residual 4-[2-(2-cyano-1-methylethylidene)hydrazino]-1-ethyl-1H-pyrazolo[3,4-b]pyridine-5-carboxylic acid, ethyl ester is recrystallized from alcohol, yield 756 g. (80%); m.p. 190°–191°.

(b)

8-ethyl-2-methyl-4H-pyrazolo[1,5-a]pyrazolo[4',3':5,6]-pyrido[3,4-e]pyrimidin-5(8H)-one 750 g. of 4-[2-(2-cyano-1-methylethylidene)hydrazino]-1-ethyl-1H-pyrazolo[3,4-e]pyridine-5-carboxylic acid, ethyl ester (2.8 mol.) are refluxed with stirring in 3 liters of acetic acid containing 50 g. of zinc chloride for 24 hours. The solution is cooled to room temperature and after the addition of about 3 liters of cold water, 8-ethyl-2-methyl-4H-pyrazolo[1,5-a]pyrazolo[4',3':5,6]pyrido[3,4-e]pyrimidin-5(8H)-one crystallizes and is filtered off. The purification of the compound is accomplished by dissolving in the theoretical amount of aqueous sodium hydroxide and acidifying the mixture with acetic acid. Yield 562 g. (75%); m.p. 285°–286° C.

(c)

2,4-dimethyl-8-ethyl-4H-pyrazolo[1,5-a]pyrazolo[4',3':5,6]pyrido[3,4-e]pyrimidin-5(8H)-one 2.7 g. of 8-ethyl-2-methyl-4-H-pyrazolo[1,5-a]pyrazolo[4',3':5,6]pyrido[3,4-e]pyrimidin-5(8H)-one (0.01 mol.) are added to a suspension of 0.03 g. of sodium hydride in 50 ml. of diethylene glycol dimethyl ether at reflux temperature. The temperature is maintained for one hour and then lowered to 120°. 2.8 g. of methyl iodide are added and heating is continued for 10 hours. The precipitated sodium iodide is filtered off, the solution evaporated to dryness and the residue recrystallized from ethyl-acetate, yield 1.9 g. (68%); m.p. 206°–207°.

EXAMPLE 2

4,8-Diethyl-2-methyl-4H-pyrazolo[1,5-a]pyrazolo[4',3':5,6]-pyrido[3,4-e]pyrimidin-5(8H)-one By substituting ethyl iodide for the methyl iodide in the procedure of Example 1(c), 4,8-dimethyl-2-methyl-4H-pyrazolo[1,5-a]pyrazolo[4',3':5,6]pyrido[3,4-e]pyrimidin-5(8H)-one is obtained in 71% yield, m.p. 178°–180° (ethyl acetate).

EXAMPLE 3

8-Ethyl-2-methyl-4-(3-methylbutyl)-4H-pyrazolo[1,5-a]pyrazolo[4',3':5,6]pyrido[3,4-e]pyrimidin-5(8H)-one By substituting 1-bromo-3-methylbutane for the methyl iodide in the procedure of Example 1(c), 8-ethyl-2-methyl-4-(3-methylbutyl)-4H-pyrazolo[1,5-a]pyrazolo[4',3':5,6]pyrido[4,3-e]pyrimidin-5(8H)-one is obtained, yield 59%, m.p. 126°–128° (ethyl acetate).

EXAMPLE 4

4-[3-(Dimethylamino)propyl]-8-ethyl-2-methyl-4H-pyrazolo[1,5-a]pyrazolo[4',3':5,6]pyrido[3,4-e]pyrimidin-5(8H)-one 5.4 g. of 8-ethyl-2-methyl-4H-pyrazolo[1,5-a]pyrazolo[4',3':5,6]pyrido[3,4-e]pyrimidin-5(8H)-one (0.02 mol.) are added to a solution of 1.5 g. of sodium methoxide in 50 ml. of diethylene glycoldimethyl-ether. The solution is refluxed with stirring for 30 minutes and then the temperature lowered to 100°. After the addition of 3 g. of dimethylaminopropyl chloride, the mixture is stirred for 24 hours. The inorganic precipitate is filtered off, the filtrate evaporated to dryness and the residue dissolved in 30 ml. of water. The aqueous solution is brought to pH 10 with sodium hydroxide and extracted three times with 50 ml. portions of diethylether. The ether layers are combined, dried with sodium sulfate and the solvent is distilled off. The residue is crystallized with ether to obtain 2.8 g. (40%) of 4-[3-(dimethylamino)-propyl]-8-ethyl-2-methyl-4H-pyrazolo[1,5-a]pyrazolo[4',3':5,6]-pyrido[3,4-e]pyrimidin-5(8H)-one, m.p. 65°–68° (propanol). Treatment of the product with acetic acid yields the acetate salt.

EXAMPLE 5

8-Ethyl-2-methyl-4-(2-morpholino)ethyl-4H-pyrazolo[1,5-a]-pyrazolo[4',3':5,6]pyrido[3,4-e]pyrimidin-5(8H)-one 2.7 g. of 8-ethyl-2-methyl-4H-pyrazolo[1,5-a]pyrazolo[4',3':5,6]pyrido[3,4-e]pyrimidin-5(8H)-one (0.01 mol.) and 0.3 g. of sodium are refluxed for 1 hour in 30 ml. of diethylene glycoldimethylether with stirring. The temperature is lowered to 90° and 2 g. of 1-chloro-2-morpholinoethane are added and stirring is continued for 24 hours. The inorganic precipitate is filtered off, the solvent removed in vacuo and the crystalline product, 8-ethyl-2-methyl-4-(2-morpholino)ethyl-4H-pyrazolo[1,5-a]pyrazolo[4',3':5,6]pyrido-[3,4-e]pyrimidin-5(8H)-one is recrystallized from ethyl acetate, yield 3.1 g. (81%); m.p. 140°–141°.

EXAMPLE 6

8-Ethyl-2-methyl-4-(2-piperidino)ethyl-4H-pyrazolo[1,5-a]-pyrazolo[4',3':5,6]pyrido[3,4-e]pyrimidin-5(8H)-one By substituting for the dimethylaminopropyl chloride in Example 4 the equivalent amount of 1-chloro-2-piperidinoethane, 8-ethyl-2-methyl-4-(2-piperidino)-ethyl-4H-pyrazolo-[1,5-a]pyrazolo[4',3':5,6]pyrido[3,4-e]pyrimidin-5(8H)-one is obtained, yield 62%; m.p. 134°–137° (ethyl acetate).

EXAMPLE 7

4-[2-(Diethylamino)ethyl]-8-ethyl-2-methyl-4H-pyrazolo[1,5-a]-pyrazolo[4',3':5,6]pyrido[3,4-e]pyrimidin-5(8H)-one By substituting for the 1-chloro-2-morpholinoethane in Example 5 the equivalent amount of 1-chloro-2-diethylaminoethane, 4-[2-(diethylamino)ethyl]-8-ethyl-2-methyl-4H-pyrazolo[1,5-a]pyrazolo[4',3':5,6-]pyrido[3,4-e]-pyrimidin-5(8H)-one is obtained, yield 63%; m.p. 90°–92° (ethyl acetate).

EXAMPLE 8

2,4-Dimethyl-4H-pyrazolo[1,5-a]pyrazolo[4',3':5,6-]pyrido-[3,4-e]pyrimidin-5(8H)-one By substituting an equivalent amount of 4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 a and continuing as in parts b and c, 2-methyl-4H-pyrazolo-[1,5-a]pyrazolo[4',3':5,6-]pyrido[3,4-e]pyrimidin-5(8H)-one and 2,4-dimethyl-4H-pyrazolo[1,5-a]pyrazolo[4',3':5,6]-pyrido[3,4-e]pyrimidin-5(8H)-one are obtained.

EXAMPLE 9

4-Butyl-8-ethyl-2-methyl-4H-pyrazolo[1,5-a]pyrazolo[4',3':5,6]-pyrido[3,4-e]pyrimidin-5(8H)-one By substituting butyl iodide for the methyl iodide in the procedure of Example 1 c, 4-butyl-8-ethyl-2-methyl-4H-pyrazolo[1,5-a]pyrazolo[4',3':5,6]pyrido[3,4-e]pyrimidin-5(8H)-one is obtained.

EXAMPLE 10

2-Methyl-4-Phenylmethyl-4H-pyrazolo[1,5-a]pyrazolo[4',3':5,6]-pyrido[3,4-e]pyrimidin-5(8H)-one By substituting the 2-methyl-4H-pyrazolo[1,5-a]pyrazolo-[4',3':5,6]pyrido[3,4-e]pyrimidin-5(8H)-one of Example 8 for the 8-ethyl-2-methyl-4H-pyrazolo[1,5-a]pyrazolo[4',3':5,6]-pyrido[3,4-e]pyrimidin-5(8H)-one and benzyl iodide for the methyl iodide in the procedure of Example 1 c, 2-methyl-4-phenylmethyl-4H-pyrazolo[1,5-a]pyrazolo[4',3':5,6]pyrido-[3,4-e]pyrimidin-5(8H)-one is obtained.

EXAMPLE 11

8-Ethyl-2-methyl-4-phenylethyl-4H-pyrazolo[1,5-a]pyrazolo-[4',3':5,6]pyrido[3,4-e]pyrimidin-5(8H)-one By substituting phenylethyl bromide for the methyl iodide in the procedure of Example 1 (c) 8-ethyl-2-methyl-4-phenylethyl-4H-pyrazolo[1,5-a]pyrazolo[4',3':5,6]pyrido-[3,4-e]pyrimidin-5(8H)-one is obtained.

EXAMPLE 12

2,4,8,10-Tetramethyl-4H-pyrazolo[1,5-a]pyrazolo[4',3':5,6]-pyrido[3,4-e]pyrimidin-5(8H)-one By substituting 1,3-dimethyl-4-hydrazino-1H-pyrazolo-[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 (a) and proceeding as in parts (b) and (c), 2,8,10-trimethyl-4H-pyrazolo[1,5-a]-pyrazolo[4',3':5,6-]pyrido[3,4-e]pyrimidin-5(8H)-one and 2,4,8,10-tetramethyl-4H-pyrazolo[1,5-a]pyrazolo[4',3':5,6]-pyrido[3,4-e]pyrimidin-5(8H)-one are obtained.

EXAMPLE 13

4-Propionyl-2,3-diethyl-8-isopropyl-4H-pyrazolo[1,5-a]pyrazolo[4',3':5,6]-pyrido[3,4-e]pyrimidin-5(8H)-one By substituting 1-isopropyl-4-hydrazino-1H-pyrazolo-[3,4-b]pyridine-5-carboxylic acid, ethyl ester for the 1-ethyl-4-hydrazino-1H-pyrazolo[3,4-b]pyridine-5-carboxylic acid, ethyl ester and 2-ethyl-3-iminopentanonitrile for the 3-iminobutyronitrile in the procedure of Example 1 (a), proceeding as in part (b) and then substituting propionyl bromide for the methyl iodide in part (c), 2,3-diethyl-8-isopropyl-4H-pyrazolo-[1,5-a]pyrazolo[4',3':5,6]pyrido[3,4-e]pyrimidin-5(8H)-one and 4-propionyl-2,3-diethyl-8-isopropyl-4H-pyrazolo[1,5-a]pyrazolo-[4',3':5,6]pyrido[3,4-e]pyrimidin-5(8H)-one, respectively, are obtained.

EXAMPLE 14

4-(4-Chlorobenzoyl)-10-ethyl-2-methyl-4H-pyrazolo[1,5-a]-pyrazolo[4',3':5,6]pyrido[3,4-e]pyrimidin-5(8H)-one By substituting 4-hydrazino-3-ethyl-1H-pyrazolo-1H-pyrazolo[3,4-b]pyridine-5-carboxylic acid propyl ester for the 1-ethyl-4-hydrazino-1H-pyrazolo[3,4-b]pyridine-5-carboxylic acid, ethyl ester in the procedure of Example 1 (a), proceeding as in part (b) and then substituting 4-chlorobenzoyl bromide for the methyl iodide in part (c), 10-ethyl-2-methyl-4H-pyrazolo[1,5-a]pyrazolo[4',3',:5,6]pyrido[3,4-e]pyrimidin-5(8H)-one and 4-(4-chlorobenzoyl)-10-ethyl-2-methyl-4H-pyrazolo[1,5-a]pyrazolo[4',3':5,6]pyrido[3,4-e]pyrimidin-5(8H)-one, respectively, are obtained.

EXAMPLE 15

4-Benzoyl-2-methyl-8-phenyl-4H-pyrazolo[1,5-a]pyrazolo-[4',3':5,6]pyrido[3,4-e]pyrimidin-5(8H)-one By substituting 4-hydrazino-1-phenyl-1H-pyrazolo-[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 (a), proceeding as in part (b) and substituting benzoyl iodide for the methyl iodide in part (c), 2-methyl-8-phenyl-4H-pyrazolo[1,5-a]pyrazolo-[4',3':5,6]pyrido[3,4-e]pyrimidin-5(8H)-one and 4-benzoyl-2-methyl-8-phenyl-4H-pyrazolo[1,5-a]pyrazolo[4',3':5,6]pyrido-[3,4-e]pyrimidin-5(8H)-one, respectively, are obtained.

EXAMPLE 16

8-Ethyl-2,4,6-trimethyl-4H-pyrazolo[1,5-a]pyrazolo[4',3':5,6]-pyrido[3,4-e]pyrimidin-5(8H)-one By substituting 1-ethyl-4-hydrazino-6-methyl-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1, 2,6-dimethyl-8-ethyl-4H-pyrazolo[1,5-a]pyrazolo[4',3':5,6]-pyrido[3,4-e]pyrimidin-5(8H)-one and 8-ethyl-2,4,6-trimethyl-4H-pyrazolo[1,5-a]pyrazolo[4',3':5,6]-pyrido[3,4-e]pyrimidin-5(8H)-one, respectively, are obtained.

EXAMPLE 17

8-Benzyl-2-methyl-4-(3-methylbutyl)-4H-pyrazolo[1,5-a]-pyrazolo[4',3':5,6]pyrido[3,4-e]pyrimidin-5(8H)-one By substituting 1-benzyl-4-hydrazino-1H-pyrazolo-[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 (a), proceeding as in part (b) and substituting 1-bromo-3-methylbutane for the methyl iodide in part (c) (as in Example 3), 8-benzyl-2-methyl-4H-pyrazolo[1,5-a]pyrazolo[4',3':5,6]pyrido[3,4-e]-pyrimidin-5(8H)-one and 8-benzyl-2-methyl-4-(3-methylbutyl)-4H-pyrazolo[1,5-a]pyrazolo[4',3':5,6]pyrido[3,4-e]pyrimidin-5(8H)-one, respectively, are obtained.

EXAMPLE 18

4-Methyl-8-phenylethyl-3-propyl-4H-pyrazolo[1,5-a]pyrazolo-[4',3':5,6]pyrido[3,4-e]pyrimidin-5(8H)-one By substituting 1-phenylethyl-4-hydrazino-1H-pyrazolo-[3,4-b]pyridine-5-carboxylic acid, methyl ester for the 1-ethyl-4-hydrazino-1H-pyrazolo[3,4-b]pyridine-5-carboxylic acid, ethyl ester and 2-iminomethylpentanonitrile for the 3-iminobutyronitrile in the procedure of Example 1 (a) and proceeding as in parts (b) and (c), 3-propyl-8-phenylethyl-4H-pyrazolo[1,5-a]pyrazolo[4',3':5,6]pyrido[3,4-e]pyrimidin-5(8H)-one and 4-methyl-8-phenylethyl-3-propyl-4H-pyrazolo-[1,5-a]pyrazolo[4',3':5,6]pyrido[3,4-e]pyrimidin-5(8H)-one, respectively, are obtained.

EXAMPLE 19

8-Ethyl-4-methyl-2-phenyl-4H-pyrazolo[1,5-a]pyrazolo[4',3':5,6]-pyrido[3,4-e]pyrimidin-5(8H)-one By substituting 3-imino-3-phenylpropionitrile for the 3-iminobutyronitrile in the procedure of Example 1 (a) and proceeding as in parts (b) and (c), 8-ethyl-2-phenyl-4H-pyrazolo-[1,5-a]pyrazolo[4',3':5,6]pyrido[3,4-e]pyrimidin-5(8H)-one and 8-ethyl-4-methyl-2-phenyl-4H-pyrazolo[1,5-a]pyrazolo-[4',3':5,6]pyrido[3,4-e]pyrimidin-5(8H)-one, respectively, are obtained.

EXAMPLE 20

4-Methyl-4H-pyrazolo[1,5-a]pyrazolo[4',3':5,6-]pyrido[3,4-e]-pyrimidin-5(8H)-one By substituting 4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester and the 3-iminopropionitrile for the 3-iminobutyronitrile in the procedure of Example 1(a) and proceeding as in parts (b) and (c), 4H-pyrazolo[1,5-a]pyrazolo[4',3':5,6]pyrido[3,4-e]pyrimidin-5(8H)-one and 4-methyl-4H-pyrazolo[1,5-a]pyrazolo[4',3':5,6-]pyrido[3,4-e]pyrimidin-5(8H)-one, respectively, are obtained.

EXAMPLE 21

8-Benzoyl-2-methyl-4-phenyl-4H-pyrazolo[1,5-a]pyrazolo[4',3':5,6]pyrido[3,4-e]pyrimidin-5(8H)-one (a)

1-Furfuryl-2-methyl-4-phenyl-4H-pyrazolo[1,5-a]pyrazolo[4',3':5,6]pyrido[3,4-e]pyrimidin-5(8H)-one By substituting 4-hydrazino-1-furfurylpyrazolo[3,4-b]pyridine-5-carboxylic acid, ethyl ester for the 1-ethyl-4-hydrazino-1H-pyrazolo[3,4-b]pyridine-5-carboxylic acid, ethyl ester in Example 1(a) and proceeding as in parts (a) and (b), 8-furfuryl-2-methyl-4H-pyrazolo[1,5-a]pyrazolo[4',3':5,6]pyrido[3,4-e]pyrimidin-5(8H)-one is obtained. This compound is now processed as in Example 1, part (c), substituting bromobenzene for the methyl iodide. A small amount of copper catalyst is added to obtain 1-furfuryl-2-methyl-4-phenyl-4H-pyrazolo[1,5-a]pyrazolo[4',3':5,6]pyrido[3,4-e]pyrimidin-5(8H)-one.

(b)

2-Methyl-4-phenyl-4H-pyrazolo[1,5-a]pyrazolo[4',3':5,6]pyrido[3,4-e]pyrimidin-5(8H)-one 0.01 ml. of 1-furfuryl-2-methyl-4-phenyl-4H-pyrazolo[1,5-a]pyrazolo[4',3':5,6]pyrido[3,4-e]pyrimidin-5(8H)-one is heated in 50 ml. of diethyleneglycol dimethyl ether containing 0.01 mol. of selenium dioxide at reflux temperature with stirring for 2 hours. The mixture is filtered hot and evaporated to dryness. Crystalline 2-methyl-4-phenyl-4H-pyrazolo[1,5-a]pyrazolo[4',3':5,6]pyrido[3,4-e]pyrimidin-5(8H)-one remains.

(c)

8-Benzoyl-2-methyl-4-phenyl-4H-pyrazolo[1,5-a]pyrazolo[4',3':5,6]pyrido[3,4-e]pyrimidin-5(8H)-one 0.01 mol. of 2-methyl-4-phenyl-4H-pyrazolo[1,5-a]pyrazolo[4',3':5,6]pyrido[3,4-e]pyrimidin-5(8H)-one and 0.02 mol. of benzoyl chloride are stirred overnight in 50 ml. of dry pyridine at room temperature. On addition of 50 ml. of water, 8-benzoyl-2-methyl-4-phenyl-4H-pyrazolo[1,5-a]pyrazolo4',3':5,6]pyrido[3,4-e]pyrimidin-5(8H)-one is filtered off.

EXAMPLE 22

2,4-Dimethyl-8-(4-methylbenzoyl)-4H-pyrazolo[1,5-a]pyrazolo[4',3':5,6]pyrido[3,4-e]pyrimidin-5(8H)-one By substituting 1-(4-methylbenzoyl)-4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 (a) and proceeding as in parts (b) and (c), 2-methyl-8-(4-methylbenzoyl)-4H-pyrazolo[1,5-a]pyrazolo[4',3':5,6]pyrido[3,4-e]pyrimidin-5(8H)-one and 2,4-dimethyl-8-(4-methylbenzoyl)-4H-pyrazolo[1,5-a]pyrazolo[4',3':5,6]pyrido[3,4-e]pyrimidin-5(8H)-one, respectively, are obtained.

EXAMPLE 23

4-(2-Aminoethyl)-2,6-dimethyl-8-ethyl-4H-pyrazolo[1,5-a]pyrazolo[4',3':5,6]pyrido[3,4-e]pyrimidin-5(8H)-one By substituting the 2,6-dimethyl-8-ethyl-4H-pyrazolo[1,5-a]pyrazolo[4',3':5,6]pyrido[3,4-e]pyrimidin-5(8H)-one obtained in Example 16 in the procedure of Example 4 and substituting 2-chloroethylamine for the dimethylaminopropyl chloride, 4-(2-aminoethyl)-2,6-dimethyl-8-ethyl-4H-pyrazolo[1,5-a]pyrazolo[4',3':5,6]pyrido[3,4-e]pyrimidin-5(8H)-one is obtained.

The hydrochloride salt is obtained by treating the above product with ethanolic HCl.

EXAMPLE 24

4-(3-Ethoxypropyl)-8-ethyl-2-methyl-4H-pyrazolo[1,5-a]pyrazolo[4',3':5,6]pyrido[3,4-e]pyrimidin-5(8H)-one By substituting 3-ethoxypropyl chloride for the dimethylaminopropyl chloride in the procedure of Example 4, 4-(3-ethoxypropyl)-8-ethyl-2-methyl-4H-pyrazolo[1,5-a]pyrazolo[4',3':5,6]pyrido[3,4-e]pyrimidin-5(8H)-one is obtained.

EXAMPLE 25

2-Methyl-4-methylthiomethyl-4H-pyrazolo[1,5-a]pyrazolo[4',3':5,6]pyrido[3,4-e]pyrimidin-5(8H)-one By substituting methylthiomethyl chloride for the dimethylaminopropyl chloride in the procedure of Example 4 and substituting the 2-methyl-4H-pyrazolo[1,5-a]pyrazolo[4',3':5,6]pyrido[3,4-e]pyrimidin-5(8H)-one obtained in Example 8 for the 8-ethyl-2-methyl-4H-pyrazolo[1,5-a]pyrazolo[4',3':5,6]pyrido[3,4-e]pyrimidin-5(8H)-one, 2-methyl-4-methylthiomethyl-4H- pyrazolo[1,5-a]pyrazolo[4',3':5,6]pyrido[3,4-e]pyrimidin-5(8H)-one is obtained.

EXAMPLE 26

8-Benzoyl-2-methyl-4-(p-methylphenyl)-4H-pyrazolo[1,5-a]pyrazolo[4',3':5,6]pyrido[3,4-e]pyrimidin-5(8H)-one By substituting p-methylphenyl bromide for the bromobenzene in the procedure of Example 21 (a), and proceeding as in parts (b) and (c), 8-benzoyl-2-methyl-4-(p-methylphenyl)-4H-pyrazolo[1,5-a]pyrazolo[4',3':5,6-]pyrido[3,4-e]pyrimidin-5(8H)-one is obtained.

EXAMPLE 27

4-[2-(Diethylamino)ethyl]-2,8,10-trimethyl-4H-pyrazolo[1,5-a]pyrazolo[4',3':5,6]pyrido[3,4-e]pyrimidin-5(8H)-one By substituting diethylaminoethyl chloride for the dimethylaminopropyl chloride and utilizing the 2,8,10-trimethyl-4H-pyrazolo[1,5-a]pyrazolo[4',3':5,6-]pyrido[3,4-e]pyrimidin-5(8H)-one product of Example 12 instead of 8-ethyl-2-methyl-4H-pyrazolo[1,5-a]pyrazolo[4',3':5,6]pyrido[3,4-e]pyrimidin-5(8H)-one in the procedure of Example 4, 4-[2-(diethylamino)ethyl]-2,8,10-trimethyl-4H-pyrazolo[1,5-a]pyrazolo[4',3':5,6]pyrido[3,4-e]pyrimidin-5(8H)-one is obtained.

EXAMPLE 28

4-Dimethylaminomethyl-2-methyl-8-phenyl-4H-pyrazolo[1,5-a]pyrazolo[4',3':5,6]pyrido[3,4-e]pyrimidin-5(8H)-one By substituting dimethylaminomethyl chloride for the dimethylaminopropyl chloride in the procedure of Example 4 and utilizing 2-methyl-8-phenyl-4H-pyrazolo[1,5-a]pyrazolo[4',3':5,6]pyrido[3,4-e]pyrimidin-5(8H)-one product of Example 15 instead of 8-ethyl-2-methyl-4H-pyrazolo[1,5-a]pyrazolo[4',3':5,6-]pyrido[3,4-e]pyrimidin-5(8H)-one, 4-dimethylaminomethyl-2-methyl-8-phenyl-4H-pyrazolo[1,5-a]pyrazolo[4',3':5,6]pyrido[3,4-e]pyrimidin-5(8H)-one is obtained.

EXAMPLE 29

8-Ethyl-2-methyl-4-(2-thiamorpholino)ethyl-4H-pyrazolo[1,5-a]pyrazolo[4',3':5,6]pyrido[3,4-e]pyrimidin-5(8H)-one Bu substituting 1-chloro-2-thiamorpholinoethane for the 1-chloro-2-morpholinoethane in the procedure of Example 5, 8-ethyl-2-methyl-4-(2-thiamorpholino)ethyl4H-pyrazolo[1,5-a]pyrazolo[4',3':5,6]pyrido[3,4-e]pyrimidin-5(8H)-one is obtained.

EXAMPLE 30

2-Methyl-4-(3-piperazino)propyl-4H-pyrazolo[1,5-a]pyrazolo[4',3':5,6]pyrido[3,4-e]pyrimidin-5(8H)-one By substituting 3-piperazinopropyl chloride for the 1-chloro-2-morpholinoethane in the procedure of Example 5 and utilizing the 2-methyl-4H-pyrazolo[1,5-a]pyrazolo[4',3':5,6]pyrido[3,4-e]pyrimidin-5(8H)-one product of Example 8, 2-methyl-4-(3-piperazino)propyl-4H-pyrazolo[1,5-a]pyrazolo[4',3':5,6]pyrido[3,4-e]pyrimidin-5(8H)-one is obtained.

EXAMPLE 31

The following ingredients are used to make 1,000 200 mg. tablets each containing 100 mg. of active ingredient:

| | |
|---|---|
| 2,4-dimethyl-3-ethyl-4H-pyrazolo-[1,5-a]pyrazolo[4',3':5,6]pyrido-[3,4-e]pyrimidine-5(8H)-one | 100 gm. |
| Polyvinyl pyrrolidone | 7.5 gm. |
| Lactose | 20 gm. |
| Magnesium stearate | 3.5 gm. |
| Corn starch | 17.5 gm. QA99 |
| Avicel (microcrystalline cellulose) | 51.5 gm. |

The medicament and lactose are thoroughly admixed. The polyvinyl pyrrolidone is dissolved in ethanol USP to make a 30% solution. This solution is used to granulate the mixture of medicament and lactose. The granulation is passed through a No. 16 screen and air dried. The dried granulation is then passed through a No. 20 screen. To the screened granulate are added the magnesium stearate, Avicel and the corn starch and the mixture is blended. The blend is then compressed into 200 mg. tablets on a standard concave punch. The tablets are then veneer coated with methyl cellulose in a spray pan.

What is claimed is:

1. A compound of the formula

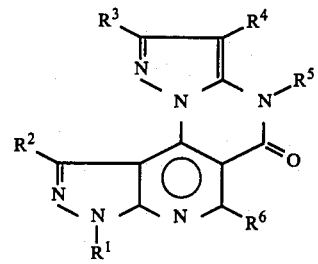

wherein
$R^1$ is hydrogen, lower alkyl, phenyl, phenyl-lower alkylene, benzoyl or substituted benzoyl;
$R^2$, $R^4$ and $R^6$ each is hydrogen or lower alkyl;
$R^3$ is hydrogen, lower alkyl or phenyl;
$R^5$ is

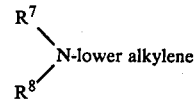

wherein $R^7$ and $R^8$ together join to complete the heterocycle piperidine, morpholine, thiamorpholine or piperazine; the substituent on said substituted benzoyl being halogen, lower alkyl or lower alkoxy,
and physiologically acceptable acid addition salts thereof.

2. A compound as in claim 1 wherein $R^1$, $R^2$, $R^3$, $R^4$ and $R^6$ each is hydrogen or lower alkyl; and $R^5$ is piperidino-lower alkylene, morpholino-lower alkylene or piperazino-lower alkylene.

3. A compound as in claim 2 wherein the lower alkyl and lower alkylene groups have up to 4 carbon atoms.

4. A compound as in claim 1 wherein $R^5$ is piperidino-lower alkylene.

5. A compound as in claim 1 wherein $R^5$ is morpholino-lower alkylene.

6. A compound as in claim 1 wherein $R^1$ is ethyl, $R^3$ is methyl and $R^2$, $R^4$ and $R^6$ each is hydrogen.

7. A compound as in claim 6 wherein $R^5$ is 2-piperidinoethyl.

8. A compound as in claim 6 wherein $R^5$ is 2-morpholinoethyl.

9. A composition comprising about 10 to 250 mg. of a compound of claim 1 and a physiologically acceptable carrier therefor.

10. A method for treating inflammatory conditions which comprises administering to a mammal suffering therefrom a composition comprising about 10 to 250 mg. of a compound of claim 1 and a physiologically acceptable carrier therefor.

* * * * *

UNITED STATES PATENT AND TRADEMARK OFFICE
CERTIFICATE OF CORRECTION

PATENT NO. : 4,127,657
DATED : November 28, 1978
INVENTOR(S) : Theodor Denzel et al.

It is certified that error appears in the above-identified patent and that said Letters Patent are hereby corrected as shown below:

In the Abstract, first line, "[4',4':5,6]" should read -- [4',3':5,6] --.

Col. 1, line 51, "The $C_1-C_4$ are" should read --The $C_1-C_4$ and--.

Signed and Sealed this

Third Day of April 1979

[SEAL]

Attest:

RUTH C. MASON
Attesting Officer

DONALD W. BANNER
Commissioner of Patents and Trademarks